US009095570B2

(12) United States Patent
Faure et al.

(10) Patent No.: US 9,095,570 B2
(45) Date of Patent: *Aug. 4, 2015

(54) LACTOFERRIN AND GUT NEURONAL HEALTH IN ADULTS AND/OR ELDERLY

(71) Applicant: NESTEC S.A., Vevey (CH)

(72) Inventors: Magali Faure, Forel (CH); Bing Wang, Tianjin (CN); Jeroen Schmitt, Moudon (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/073,522

(22) Filed: Nov. 6, 2013

(65) Prior Publication Data

US 2014/0135262 A1    May 15, 2014

Related U.S. Application Data

(63) Continuation of application No. 13/319,656, filed as application No. PCT/EP2010/056238 on May 7, 2010, now Pat. No. 8,592,369.

(30) Foreign Application Priority Data

May 12, 2009   (EP) ...................... 09159964

(51) Int. Cl.
| | | |
|---|---|---|
| A61K 38/00 | (2006.01) | |
| A61P 3/02 | (2006.01) | |
| A61K 38/40 | (2006.01) | |
| A23L 1/29 | (2006.01) | |
| A23L 1/305 | (2006.01) | |
| A23L 2/66 | (2006.01) | |
| A61K 35/20 | (2006.01) | |

(52) U.S. Cl.
CPC ................ *A61K 38/40* (2013.01); *A23L 1/296* (2013.01); *A23L 1/3056* (2013.01); *A23L 2/66* (2013.01); *A61K 35/20* (2013.01); *A23V 2002/00* (2013.01)

(58) Field of Classification Search
CPC ....... A61K 38/40; A61K 35/20; A61K 33/00; A61K 38/1709; A61K 38/17; A61K 38/57
See application file for complete search history.

(56) References Cited

U.S. PATENT DOCUMENTS

| | | | |
|---|---|---|---|
| 4,977,137 A | 12/1990 | Nichols et al. | |
| 6,787,158 B1 | 9/2004 | Erdmann et al. | |
| 2002/0004073 A1 | 1/2002 | Gohlke et al. | |
| 2006/0068022 A1* | 3/2006 | Playford | 424/535 |
| 2007/0009609 A1 | 1/2007 | Gohlke et al. | |
| 2007/0036873 A1* | 2/2007 | Ghosal | 424/725 |

FOREIGN PATENT DOCUMENTS

| | | |
|---|---|---|
| EP | 322589 | 7/1989 |
| EP | 880902 | 12/1998 |
| IE | 20060795 | 5/2007 |
| JP | 8038044 | 2/1996 |
| JP | 2006006257 | 1/2006 |
| WO | 0111990 | 2/2001 |
| WO | 2006085143 | 8/2006 |
| WO | 2007145520 | 12/2007 |
| WO | 2008018103 | 2/2008 |

OTHER PUBLICATIONS

The Michael Stern Parkinson's Research Foundation, 2013, available on-line at http://www.parkinsoninfo.org/about-parkinsons-disease/.*
DHHS publication, National Vital Statistics Reports, 2012, vol. 61, No. 3.*
Raiten et al., "Executive Summary for the Report: Assessment of Nutrient Requirements for Infant Formulas", Life Sciences Research Office, American Society for Nutritional Sciences, The Journal of Nutrition, vol. 128, No. 11S, pp. 2059S-2294S (28 pages), 1998.
PCT International Search Report for Application No. PCT/EP2010/056238 mailed on Jun. 24, 2010.
Nakajima M et al: "Lactoferrin as a suppressor of cell migration of gastrointestinal cell lines"; Journal of Cellular Physiology, vol. 170, no. 2, Feb. 1997, pp. 101-105; XP002548907.
Postuma R.B et al: "Effects of the amyloid protein precursor of Alzheimer's disease and other ligands of the LDL receptor-related-protein on neurite outgrowth from sympathetic-neurons in culture"; FEBS Letters, vol. 428, No. 1-2, May 22, 1998, pp. 13-16; XP004257902.
Togawa J -I et al: "Lactoferrin reduces colitis in rats via modulation of the immune system and correction of cytokine imbalance"; American Journal of Physiology—Gastrointestinal and Liver Physiology 2002; vol. 283, No. 1, 2002, pp. G187-G195; XP002548908.
Troost F J et al: "Orally ingested human lactoferrin is digested and secreted in the upper gastrointestinal tract in vivo in women with ileostomies"; Journal of Nutrition, vol. 132, No. 9, Sep. 2002, pp. 2597-2600; XP002548910.
Haversen L A et al; "Anti-Inflammatory Activities of Human Lactoferrin in Acute Dextran Sulphate-Induced Colitis in Mice", Scandinavian Journal of Immunology, vol. 57, No. 1, Jan. 2003, pp. 2-10; XP002548909.
Yamaguchi, P.: "The leader of the pack"; Functional Ingredients, [Online] 2004, pp. 1-6; XP002548904; Internet; Retrieved from the Internet: www.functionalingredientsmag.com/content/print. aspx?topic=the-leader-of-the-pack, p. 4, paragraphs 5, 6.

(Continued)

*Primary Examiner* — Marcela M Cordero Garcia
*Assistant Examiner* — Kaipeen Yang
(74) *Attorney, Agent, or Firm* — K&L Gates LLP (57) ABSTRACT

The present invention relates generally to the field of neuronal health and neuronal protection. One embodiment of the present invention relates to a composition that can be used for the protection of the enteric nervous system from neurodegeneration. Disorders linked to an impaired enteric nervous system can be treated or prevented by the administration of lactoferrin containing compositions according to the present invention.

6 Claims, 9 Drawing Sheets

(56) References Cited

OTHER PUBLICATIONS

Ward P P et al: "Multifunctional roles of lactoferrin: A critical overview"; Cellular and Molecular. Lifesciences, vol. 62, No. 22, Nov. 2005, pp. 2540-2548; XP002548905.

Lin et al: "Human lactoferrin exerts bi-directional actions on PC12 cell survival via ERK1/2 pathway"; Biochemical and Biophysical Research Communications, vol. 337, No. 1, Nov. 11, 2005, pp. 330-336; XP005093452.

Lönnerdal Bo: "Nutritional roles of lactoferrin"; Current Opinion in Clinical Nutrition and Metabolic Care, vol. 12, No. 3, May 1, 2009, pp. 293-297; XP008105975.

Otsuki K et al: "Effect of enteric-coated lactoferrin on constipation during pregnancy"; Biochemistry and Cell Biology, vol. 84, No. 3, Jun. 2006; XP008112904.

Shoji H et al: "Effects of iron-unsaturated human lactoferrin on hydrogen peroxide-induced oxidative damage in intestinal epithelial cells"; Pediatric Research, vol. 61, No. 1, Jan. 2007, pp. 89-92; XP002548906.

Lin et al: "Bovine lactoferrin protects RSC96 Schwann cells from tumor necrosis factor-alpha-induced growth arrest via extracellular-signal-regulated kinase 1/2"; Neuroscience, vol. 151, No. 2, Oct. 30, 2007, pp. 396-402; XP022416156.

* cited by examiner

LACTOFERRIN AND GUT NEURONAL HEALTH IN ADULTS AND/OR ELDERLY

PRIORITY CLAIM

This application is a continuation application of U.S. patent application Ser. No. 13/319,656, filed on Jan. 12, 2012, which is the National Stage of International Application No. PCT/EP2010/056238, filed May 7, 2010, which claims priority to European Application No. 09159964.7, filed May 12, 2009, the entire contents of which are being incorporated herein by reference.

FIELD OF THE INVENTION

The present invention relates generally to the field of neuronal health and neuronal protection. One embodiment of the present invention relates to a composition that can be used for the protection and/or repair of the enteric nervous system. Disorders linked to an impaired enteric nervous system can be treated or prevented by the administration of lactoferrin containing compositions according to the present invention.

BACKGROUND

The nervous system is a highly complex network composed of neuronal and glial cells. It is present in all mammalian species. The nervous system is composed of the central nervous system (brain and spinal cord) and the peripheral nervous system (somatic, autonomous and enteric nervous system). The central nervous system drives the cognitive functions (memory, attention, perception, action, etc).

The central nervous system drives the cognitive functions (memory, attention, perception, action, etc). Together with the peripheral nervous system, it has a fundamental role in the control of behaviour. The somatic nervous system is responsible for coordinating the body's movements (under conscious control). The autonomous nervous system maintains homeostasis in the body activities without conscious control (heart rate, etc). Finally, and part of this latest, the enteric nervous system, which directly controls the gastrointestinal tract functions such as the intestinal barrier, the motility, the absorption, the digestion and the secretions, contributing as such to the protection of the intestine from any type and to digestive comfort.

The nervous system develops during gestation and then refines to a mature, functional network during the post natal period.

With ageing, or in any pathological situations accompanied by intestinal neuropathies (e.g., diabetes, intestinal inflammation such as IBD, IBS, Parkinson's disease, intestinal mucositis associated to chemotherapy treatment, etc), the nervous system in the gut is challenged by environmental factors or by stress, for example, and neuronal losses occur. An impaired enteral nervous system may result.

Such an impaired enteral nervous system may lead to intestinal dysfunctions, such as a low digestive/absorptive capacity contributing to malnutrition, intestinal dismotility (from a slower intestinal transit to constipation or to chronic intestinal pseudoobstruction), a weak intestinal barrier function, enteral feeding intolerance (therefore need of parenteral nutritional support), gut discomfort with harder stools, and increased infection risks.

It was an object of the present invention to improve the state of the art and to provide a composition that is based on natural ingredients and that allows protecting the nervous system in the gut.

This object was achieved by the subject matter of the independent claims.

The present inventors were able to demonstrate that lactoferrin, for example a composition supplemented with lactoferrin, can be used to protect intestinal neuronal cells.

Furthermore, the present inventors were able to demonstrate that lactoferrin, for example a composition supplemented with lactoferrin, can be used to promote neuronal growth which may favour neuronal repair processes.

It could further be shown that the administration of lactoferrin allows it to increase the neuron density and neuron survival.

Lactoferrin (LF), also known as lactotransferrin (LTF), is a globular multifunctional protein that is known to exhibit an antimicrobial activity and is a part of the innate defence, mainly at mucoses.

Lactoferrin may be found for example in milk and whey and in many mucosal secretions such as tears and saliva. As such, Lactoferrin may be purified, e.g., from milk or may be produced recombinantly.

The present invention relates to lactoferrin obtainable from any source.

Lactoferrin from milk or whey, for example, has the advantage that it is a natural ingredient obtained from a food-grade composition and can consequently be used as enriched fraction of the food composition without further purification.

Recombinantly obtained lactoferrin has the advantage that it can be produced easily in high concentrations.

Human colostrum has a relatively high concentration of lactoferrin, followed by human milk, then cow milk.

The present inventors have found that lactoferrin or lactoferrin enriched compositions may be used to protect neuronal cells against degeneration. Such degeneration may follow, for example, any stress associated to situations or pathologies listed before. Lactoferrin was found to promote neuronal survival and/or limit or prevent neuronal death of intestinal neuronal cells, and to promote neuronal growth which is important for repair processes.

In adults or in the elderly the lactoferrin and/or the lactoferrin containing compositions of the present inventions may be used to protect the nervous system from any stress, and—consequently—to limit and/or prevent stress-induced intestinal neuronal dysfunctions.

For the purpose of the present invention, the term "adults" includes people over the age of 18.

A subject is considered as "elderly" if it has surpassed the first half of its average expected lifespan in its country of origin, preferably, if it has surpassed the first two thirds of the average expected lifespan in its country of origin, more preferably if it has surpassed the first three quarters of the average expected lifespan in its country of origin, most preferred if it has surpassed the first four fifths of the average expected lifespan in its country of origin.

Lactoferrin and/or the composition of the present invention may be administered, for example, to
- adults
- elderly people
- any adult or elderly person showing intestinal neuropathies associated to any type of physiological or pathological conditions and/or
- any adult or elderly person showing intestinal dysfunctions (digestive disorders, gastrointestinal motility disorders, gastrointestinal reflux, constipation, fecal incontinence, oral feeding intolerance, parenteral feeding), Bowel obstruction pathologies.

Consequently, one embodiment of the present invention is an ingestible composition enriched in lactoferrin.

Enriched means that lactoferrin was either added to the composition, so that the resulting lactoferrin content of the composition is higher than the lactoferrin content of the composition without lactoferrin addition, or that the composition was treated in a way to concentrate the natural lactoferrin content in a composition.

Lactoferrin may also be provided as pure compound.

Alternatively, lactoferrin may be provided as a lactoferrin enriched fraction, for example a lactoferrin enriched milk or whey fraction.

As milk or whey source bovine milk, human milk, goat milk, camel milk, horse milk and/or donkey milk may be used, for example. Colostrum may be used as well.

In therapeutic applications, compositions are administered in an amount sufficient to at least partially cure or arrest the symptoms of the disorder and/or its complications. An amount adequate to accomplish this is defined as "a therapeutically effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

Lactoferrin may be administered in the framework of the present invention in a therapeutically effective dose and/or in a prophylactic effective dose.

Typical lactoferrin enriched compositions may comprise lactoferrin in an amount of at least 1.6 g/L.

For example, the composition of the present invention may contain lactoferrin in a concentration of at least 0.75% (w/w), preferably at least 1% (w/w).

In one embodiment, the composition is to be administered in an amount corresponding to an ingestion of at least 0.25 g lactoferrin, preferably at least 0.5 g lactoferrin more preferably at least 1 g lactoferrin per day per kg body weight.

For example, the composition may be consumed in an amount corresponding to at least 1 g lactoferrin/kg body weight/day intake for pregnant and/or lactating mothers.

Lactoferrin may be present in the composition in a concentration of at least 0.01 g per 100 kcal, preferably of at least 0.1 g per 100 kcal. For example, lactoferrin may be present in the composition in the range of about 0.01 g-100 g, preferably 0.1 g-50 g, even more preferred 2 g-25 g per 100 kcal of the composition.

Lactoferrin may also be used in combination with other compounds, such as sialic acid and/or iron, for example.

Sialic acid is a generic term for the N- or O-substituted derivatives of neuraminic acid, a monosaccharide with a nine-carbon backbone.

Any sialic acid may be used for the purposes of the present invention. However, it is preferred if the sialic acid has the following formula R1 = H, acetyl, lactyl, methyl, sulfate, phosphate, anhydro, sialic acid, fucose, glucose, or galactose
R2 = N-acetyl, N=glycolyl, amino, hydroxyl, N-glycolyl-O-acetyl, or N-glycolyl-O-methyl
R3 = H, galactose, N-acetylglucosamine, N-acetylgalactosamine, sialic acid, or N-glycolylneuraminic acid R1 may be selected from the group consisting of H, acetyl, lactyl, methyl, sulfate, phosphate, anhydrosialic acid, fucose, glucose and/or galactose.

R2 may be selected from the group consisting of N-acetyl, N-glycolyl, amino, hydroxyl, N-glycolyl-O-acetyl, and/or N-glycolyl-O-methyl.

R3 may be selected from the group consisting of H, galactose, N-acetylglucosime, N-acetylgalactosamine, sialic acid, and/or n-glycolylneuraminic acid.

The groups in position R1 may be identical or may differ from each other.

For example, the sialic acid may be N-acetylneuraminic acid with R1=H, R2=N-acetyl and R3=H. According to a further embodiment of the present invention the sialic acid may selected from the group consisting of 2-keto-5-acetamido-3,5-dideoxy-d-glycero-d-galactononulosonic acid (Neu5Ac) or mixtures thereof.

Sialic acid as used in the present invention comprises N-Acetylneuraminic acid, which has the following synonyms and abbreviations: o-Sialic acid; 5-Acetamido-3,5-dideoxy-D-glycero-D-galacto-2-nonulosonic acid; 5-Acetamido-3,5-dideoxy-D-glycero-D-galactonulosonic acid; Aceneuramic acid; N-acetyl-neuraminate; N-Acetylneuraminic acid; NANA, and Neu5Ac.

A particular preferred lactoferrin containing composition may contain sialic acid in an amount in the range of 100 mg/100 g (w/w) to 1000 mg/100 g (w/w) of the composition, for example in the range of 500 mg/100 g (w/w) to 650 mg/100 g (w/w) of the composition.

The composition of the present invention may for example comprise at least about 0.001 weight-% sialic acid. In further embodiments of the present invention, the composition may comprise at least about 0.005 weight-%, or at least about 0.01 weight-% of sialic acid.

Alternatively or additionally the lactoferrin containing composition may contain iron in an amount in the range of about 1 mg/100 g (w/w) to 50 mg/100 g (w/w) of the composition, for example 10 mg/100 g (w/w) to 30 mg/100 g (w/w) of the composition.

One lactoferrin containing composition may contain for example about 580 mg/100 g (w/w) sialic acid and 22 mg/100 g (w/w) iron.

The lactoferrin containing composition of the present invention may have a caloric density in the range of 30 kcal/100 g-1000 kcal/100 g of the composition, preferably 50 kcal/100 g-450 kcal/100 g of the composition. It may for example have a caloric density of about 400 kcal/100 g.

The nature of the composition is not particularly limited. It is preferably a composition for oral, enteral or parenteral administration.

The composition may be for example selected from the group consisting of food products, animal food products, pharmaceutical compositions, nutritional formulations, nutraceuticals, drinks, food additives, nutritional supplements, and feeding formulas for elderly people.

In one typical embodiment of the present invention, the composition will contain a protein source, a lipid source and a carbohydrate source.

For parenteral application forms, it may be preferred that the composition does not contain simultaneously a protein source, a lipid source and a carbohydrate source. Instead, during parenteral administration the carbohydrate source is administered separately from the protein and/or lipid source to reduce the risk of clogging.

The composition comprises a protein source which may be present in the range of between 1.4 and 100 g/100 kcal, preferably between 2 and 6 g/100 kcal of the composition. Since lactoferrin is a protein it should be considered a part of the protein source.

The type of protein is not believed to be critical to the present invention. Thus, protein sources based on whey, casein and mixtures thereof may be used, for example. As far as whey proteins are concerned, acid whey or sweet whey or mixtures thereof may be used as well as alpha-lactalbumin and beta-lactoglobulin in whatever proportions are desired. The whey protein may be modified sweet whey. Sweet whey is a readily available by-product of cheese making and is frequently used in the manufacture of nutritional formulas based on cows' milk. However, sweet whey includes a component which is undesirably rich in threonine and poor in tryptophan called caseino-glyco-macropeptide (CGMP). Removal of the CGMP from sweet whey results in a protein with a threonine content closer to that of human milk. This modified sweet whey may then be supplemented with those amino acids in respect of which it has a low content (principally histidine and tryptophan). A process for removing CGMP from sweet whey is described in EP 880902 and a nutritional formula based on this modified sweet whey is described in WO 01/11990. The proteins may be intact or hydrolysed or a mixture of intact and hydrolysed proteins. It may be desirable to supply partially hydrolysed proteins (degree of hydrolysis between 2 and 20%), for example for subjects believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in two steps as described in EP 322589. For an extensively hydrolysed protein, the whey proteins may be subjected to triple hydrolysis using Alcalase 2.4 L (EC 940459), then Neutrase 0.5 L (obtainable from Novo Nordisk Ferment AG) and then pancreatin at 55° C. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

Whey protein is known to provide several health benefits. For example, it is easily digestible. The protein fraction in whey (approximately 10% of the total dry solids within whey) comprises several protein fractions, for example beta-lactoglobulin, alpha-lactalbumin, bovine serum albumin and immunoglobulins. In one embodiment at least 50%, preferably at least 75%, even more preferred at least 85% by weight of the protein source is whey protein.

The compositions of the present invention may contain a lipid source. The lipid source may be any lipid or. Preferred fat sources include milk fat, palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The lipid source preferably has a ratio of n–6 to n–3 fatty acids of about 5:1 to about 15:1; for example about 8:1 to about 10:1.

If present, the lipid source may contribute to between 30 to 55% of the total energy of the composition.

The compositions of the present invention may contain a carbohydrate source. Any carbohydrate source may be used, such as lactose, saccharose, maltodextrin, starch and mixtures thereof.

A carbohydrate source may contribute to between 35 and 65% of the total energy of the composition.

For example a composition of the present invention may comprise protein in the range of about 1.8 to 3.0 g/100 kcal, lipids in the range of about 4.4 to 6.5 g/100 kcal and/or carbohydrates in the range of about 1.7 to 12 g/100 kcal.

If the composition is liquid, its energy density may be between 60 and 75 kcal/100 ml.

If the composition is solid, its energy density may be between 60 and 75 kcal/100 g.

The compositions of the present invention may also contain all vitamins and minerals understood to be essential in the daily diet and in nutritionally significant amounts. Minimum requirements have been established for certain vitamins and minerals. Examples of minerals, vitamins and other nutrients optionally present in the composition include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the numerous factors, such as age weight and condition of the person or animal the composition is administered to.

The compositions may also comprise at least one probiotic bacterial strain. A probiotic is a microbial cell preparation or components of microbial cells with a beneficial effect on the health or well-being of the host. Suitable probiotic bacterial strains include *Lactobacillus rhamnosus* ATCC 53103 obtainable from Valio Oy of Finland under the trade mark LGG, *Lactobacillus rhamnosus* CGMCC 1.3724, *Lactobacillus paracasei* CNCM 1-2116, *Lactobacillus reuteri* ATCC 55730 and *Lactobacillus reuteri* DSM 17938 obtainable from BioGaia AB, *Bifidobacterium lactis* CNCM 1-3446 sold inter alia by the Christian Hansen company of Denmark under the trade mark Bb12 and *Bifidobacterium longum* ATCC BAA-999 sold by Morinaga Milk Industry Co. Ltd. of Japan under the trade mark BB536. The amount of probiotic, if present, likewise preferably varies as a function of the age of the person or animal. Generally speaking, the probiotic content may increase with increasing age of the person for example from $10^3$ to $10^{12}$ cfu/g formula, more preferably between $10^4$ and $10^8$ cfu/g composition (dry weight).

The compositions may also contain at least one prebiotic in an amount of 0.3 to 10%. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®.

A particularly preferred prebiotic is a mixture of galacto-oligosaccharide(s), N-acetylated oligosaccharide(s) and sialylated oligosaccharide(s) in which the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. This mixture is hereinafter referred to as "CMOS-GOS". Preferably, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide.

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1, 3Galβ1,4Glc, Galβ1,6Galβ1,6Galβ1,4Glc, Galβ1,6Galβ1, 3Galβ1,4Glc and Galβ1,3Galβ1,6Galβ1,4Glc, Galβ1, 4Galβ1,4Glc and Galβ1,4Galβ1,4Galβ1,4Glc and mixtures thereof are commercially available under the trade marks Vivinal® and Elix'Or®. Other suppliers of oligosaccharides are Dextra Laboratories, Sigma-Aldrich Chemie GmbH and Kyowa Hakko Kogyo Co., Ltd. Alternatively, specific glycosyltransferases, such as galactosyltransferases may be used to produce neutral oligosaccharides.

Suitable sialylated oligosaccharides include NeuAcα2, 3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

The compositions may optionally contain other substances which may have a beneficial effect, such as nucleotides, nucleosides, and the like.

The compositions for use in the invention may be prepared in any suitable manner. For example, a nutritional formula may be prepared by blending together the protein source, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger. The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point. The homogenised mixture is transferred to a suitable drying apparatus such as a spray drier or freeze drier and converted to powder. The powder should have a moisture content of less than about 5% by weight. If it is desired to add probiotic(s), they may be cultured according to any suitable method and prepared for addition to the nutritional formula by freeze-drying or spray-drying for example. Alternatively, bacterial preparations can be bought from specialist suppliers such as Christian Hansen and Morinaga already prepared in a suitable form for addition to food products. Such bacterial preparations may be added to the powdered nutritional formula by dry mixing.

Lactoferrin may be added at any stage during this procedure, but is preferably added after the heating step.

The present invention extends to the use of lactoferrin for the preparation of a composition for the protection of the enteric nervous system; as well as for the treatment and/or prevention of disorders linked to an impaired enteric nervous system.

Disorders associated to intestinal neuropathies, and therefore to an impaired enteric nervous system include for example a low digestive and/or absorptive capacity contributing to malnutrition, gastrointestinal reflux, intestinal dismotility (from a slower intestinal transit to constipation or chronic intestinal pseudoobstruction, fecal incontinence), gastrointestinal reflux, a weak intestinal barrier function, enteral feeding intolerance (therefore need of parenteral nutritional support), gut discomfort with harder stools, and increased infection risks.

In another embodiment of the present invention, the lactoferrin containing composition may be used to treat or prevent a delayed neural migration.

The composition of the present invention can be used to increase the neuronal density and or the neuronal survival.

For the uses of the present invention it is essential that the composition contains lactoferrin or a compound that yields lactoferrin after consumption. The composition does not have to be enriched in lactoferrin, although this may be preferable, since this way more lactoferrin can be administered in smaller volumes.

The lactoferrin may be used to prepare any kind of composition. It is preferred, however, that the lactoferrin is provided as a composition in accordance with what is described above.

The composition may be administered to adults and/or to the elderly.

Those skilled in the art will understand that they can freely combine all features of the present invention described herein, without departing from the scope of the invention as disclosed. In particular, features described for the uses of the present invention may be applied to composition of the present invention and/or to lactoferrin and vice versa.

Further advantages and features of the present invention are apparent from the following Examples and Figures.

DETAILED DESCRIPTION

Examples

Biological activity of lactoferrin enriched bovine milk fraction: Effect on neurite outgrowth in vitro.

The neurite outgrowth process comprises the outgrowth of axons from neurons and is part of neuronal development. The impact of a fraction of bovine milk enriched in lactoferrin on neurite outgrowth was measured using a well established and commonly used in vitro bioassay.

Briefly, NS20Y murine neuroblastoma cells (DSMZ) were thawed from cryogenic storage, plated at a density of approximately $27 \times 10^3$ cells per $cm^2$ in tissue culture-treated flasks (Falcon) and expanded in the presence of DMEM (Gibco) containing 10% FCS (Gibco) and 2 mM L-glutamine (Gibco). Two days after plating, the cells were detached from the flask by mechanical agitation (tapping of the flask), and a single cell suspension was obtained by passing the suspension several times through a flame-polished glass pipette. Cells were then plated onto 13 mm round glass coverslips in the presence of DMEM containing 10% FCS and 2 mM L-glutamine at a density of 2,000 cells per coverslip. The following day the medium was switched to DMEM containing 0.5% FCS, 2 mM L-glutamine, and different concentrations of the milk fractions to be tested. One day later cells were fixed with 4% paraformaldehyde and the coverslips mounted on slides.

All coverslips were imaged with an Axioplan 2 microscope (Zeiss). Digital images were taken from 25 defined fields across the diameter of the coverslip (20× objective, Axiocam MRc, Zeiss). Cells were counted systematically from the first field at the edge of the coverslip across the coverslip until 100 cells had been counted. Cells were scored for either positive or negative for neurite outgrowth. Positive cells for neurite outgrowth were considered if the axon-resembling projections emanating from the cell body reached a length greater than the cell body.

A student t test was used to compare differences in the mean between one control reference population and means from all other treatments in each group.

Figure 1:
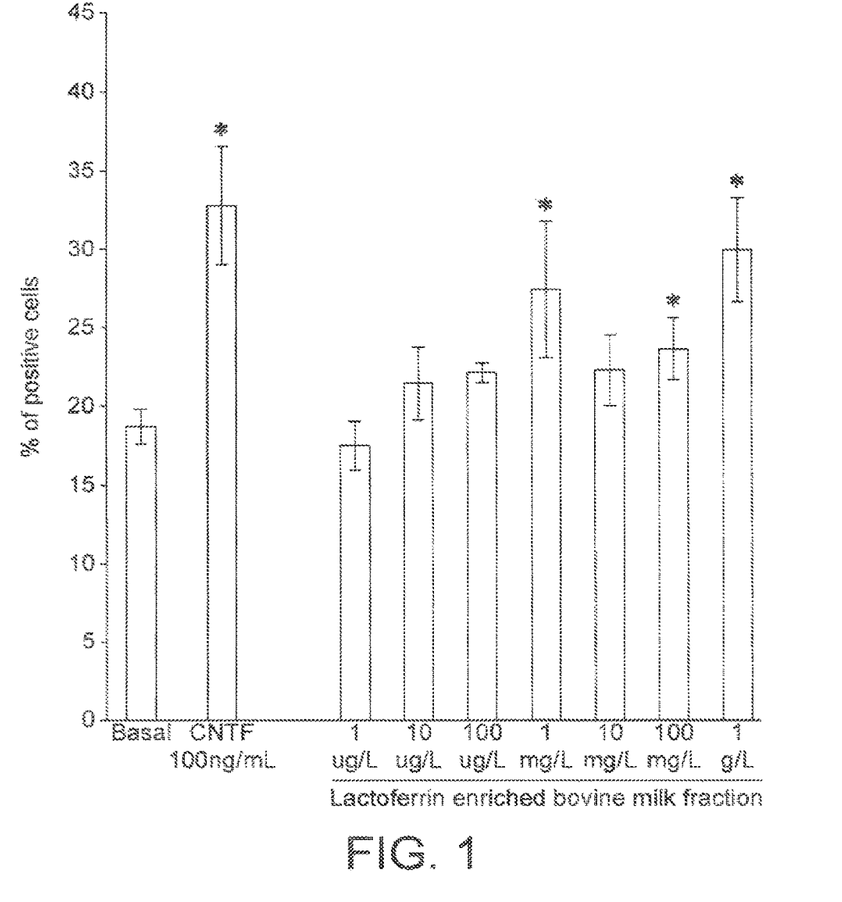
FIG. 1 shows the percentage of positive NS20Y cells for neurite outgrowth in basal condition (untreated cells) and after treatment of the cells with either the neurotrophic factor CNTF (100 ng/mL) or the lactoferrin enriched bovine milk fraction at different concentrations. Data are means±SEM, n=3 to 7 according to the group (Basal, n=7; CNTF, n=3; 1 ug/L, n=3; 10 ug/L, n=7; 100 ug/L, n=3; 1 mg/L, n=3; 10 mg/L, n=5; 100 mg/L, n=7; 1 g/L, n=6). Data were compared to the basal untreated group with the student t test. A difference was considered significant when P<0.05.

The following concentrations of the lactoferrin enriched bovine milk fraction were tested: 1 µg/L, 10 µg/L, 100 µg/L, 1 mg/L, 10 mg/L, 100 mg/L, and 1 g/L. A positive control (CNTF, ciliary neurotrophic factor, 100 ng/mL), which is a well known neurotrophic factor previously reported to promote neurite outgrowth of different neuronal populations (Oyesiku and Wigston, 1996 (Oyesiku N M, Wigston D J: Ciliary neurotrophic factor stimulates neunte outgrowth from spinal cord neu-rons. J Comp Neurol 1996; 364: 68-77)) was performed. A basal control consisted of untreated cells. Results are shown in FIG. 1.

Protection of Neuronal Cells Against Stress

Figure 2:
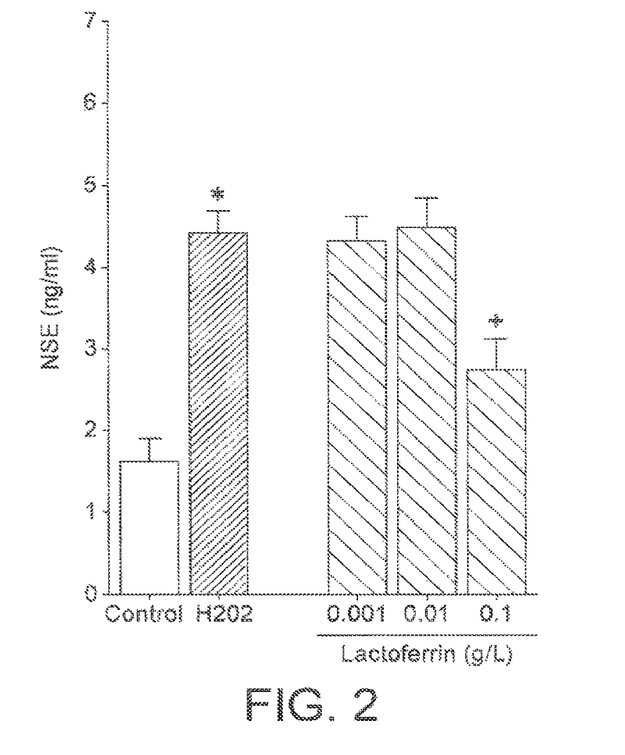
FIG. 2 shows the release of neuron-specific enolase (NSE), a marker for neuronal cell death, by a primary culture of enteric neurons, following $H_2O_2$ challenge and prevention with bovine milk Lactoferrin. Data are mean±SEM, n=8. A difference was considered significant when P<0.05

Rat primary cultures of enteric neuronal cells were seeded into wells and incubated with different concentrations of bovine lactoferrin-enriched fraction for 48 h. After washing three times with phosphate buffer saline (sterile PBS, 37° C.), the cells were incubated for 12 hours in cell medium without lactoferrin and containing $H_2O_2$ or its vehicle (control). The protective effect of lactoferrin upon $H_2O_2$-induced neuronal cell death was evaluated by measuring the release of neuron-specific enolase (NSE) in the cell medium. After oxidative stress, the medium of the different groups were collected and centrifuged for 10 min at 12,000 rpm (4° C.). The supernatant was collected and the NSE released in the culture medium was quantified by immunoradiometric assay. Results are expressed in ng/mL. As shown on FIG. 2, $H_2O_2$ induced a significant increase of NSE in the medium ($p<0.05$, $n=8$). Treatment of primary neuronal enteric cells with lactoferrin-enriched fraction significantly prevented the $H_2O_2$-induced release of NSE ($p<0.05$, $n=8$) as shown on FIG. 2.

Figure 3:
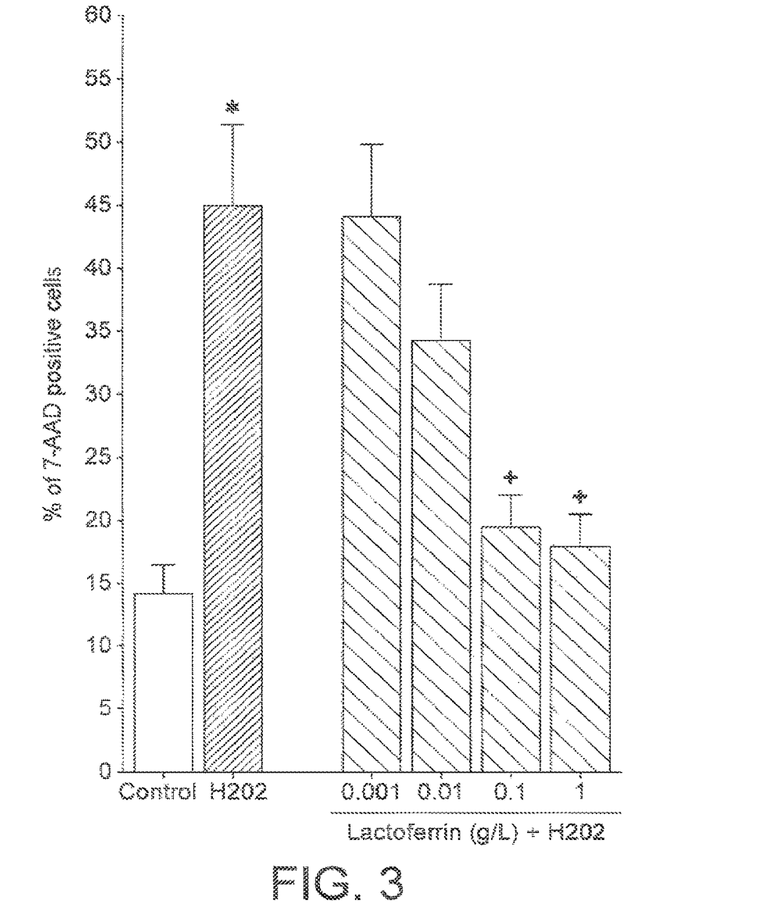
FIG. 3 shows the percentage of 7-AAD positive cells in cultured SH-SY5Y cells, following $H_2O_2$ challenge in presence or not of different concentrations of bovine milk Lactoferrin ranging from 0.001 to 1 g/L.

The neuroprotective property of bovine lactoferrin was confirmed using a human neuronal-like cell line (SH-SY5Y-neuroblastoma cells). Briefly, SH-SY5Y cells were plated for 24 h, and bovine lactoferrin-enriched fraction was added to the culture media of cells at different concentrations for the following 48 h. $H_2O_2$ for 6 h or with its vehicle (control) directly added to the cell media. Cells were finally washed with 0.1 M PBS before being harvested with trypsine-EDTA. Cell suspension was then pooled with the supernatant and centrifuged for 5 min at 2,000 rpm. After centrifugation, the pellet was resuspended in 500 microliter of PBS 0.1M. Membrane permeability was evaluated by flow cytometry using the 7-AAD as fluorescent marker. For this, 200 microliter of cell suspension were incubated with 7-AAD for 10 min before acquisition using BD FACS Array™ bioanalyser. This flow cytometric assay using 7-aminoactinomycin D (7-AAD) allowed to distinguish live (7-AAD negative) and late apoptotic/necrotic (7-AAD positive) SH-SY5Y cells in response to oxidative stress. Results as presented in FIG. 3 were expressed as percentage of 7-AAD positive cells per total number of cells. As shown in FIG. 3, $H_2O_2$ induced a significant increase in the percentage of 7-AAD positive cells ($p<0.05$, $n=6$). Treatment of SH-SY5Y cells with lactoferrin prevented the $H_2O_2$-induced increase in percentage of 7-ADD positive cells, as shown on FIG. 3.

Lactoferrin Improves Neuron Density and Neuron Survival

A morphological examination was conducted following MR acquisition. Contiguous sections at the level of the striatum, dorsal and lateral hippocampus were collected to assess cortical and hippocampal architecture and white matter injury. Specific cells types were labeled using immunohistochemistry, in order to determine specific cellular responses. Specific labeling of neurons (NeuN), astrocytes (GFAP) and radial glia (Nestin), in conjunction with markers of white matter myelination (MBP), was performed. The brief methodology was the followings:

At P7 and P21, respectively, pups from each group were deeply anesthetized using ketalar (50 mg/ml; 0.2-0.5 ml, i.p.). Animals were perfused intracardially with 0.9% NaCl, then 4% paraformaldehyde. Brains were removed, weighed and postfixed in 4% paraformaldehyde overnight, then 30% sucrose for 24 h minimum, and stored at −80° C. until sectioned. Coronal sections (10 μm) at the level of the dorsal hippocampus were cut on a cryostat (Microm Cryo-Star HM 560M, Microm International, Germany). Three sections at 200 μm intervals were collected from each animal.

Immunohistochemistry: Brain tissue was processed for immunoreactivity to MBP (1:400 brand city country) using the avidin-biotin peroxidase complex (ABC; Vector Laboratories, Burlingame, Calif., USA). Sections were blocked in 4% bovine serum albumin (BSA brand city country), then incubated with the primary antibody for 24 h at 4° C., after which they were incubated with the secondary antibody (1:200 brand city country), then with the avidin-biotin complex (1:200, Vector Laboratories, Burlingame, Calif., USA). Sections were reacted with the chromagen, 3,3-diaminobenzidine (DAB brand city country) in 0.01% hydrogen peroxide, then coverslipped.

The same protocol was used for fluorescence immunohistochemistry for nestin (1:500 brand city country), GFAP (1:400 brand city country), and NeuN (1:200 brand city country), except that sections were not incubated in the avidin-biotin complex and DAB.

Each experimental group and their respective controls were stained simultaneously. When the primary antibody treatment was omitted, staining failed to occur.

Quantitative analyses were performed using MetaMorph® Imaging System (Meta Imaging Software, Molecular Devices Corporation, Pennsylvania, U.S.A.). Values for each animal were pooled and a mean of means±SEM was calculated for each group. Measurements were made on coded slides blinded to the observer with the codes not being disclosed until the conclusion of analyses.

Figure 4A:
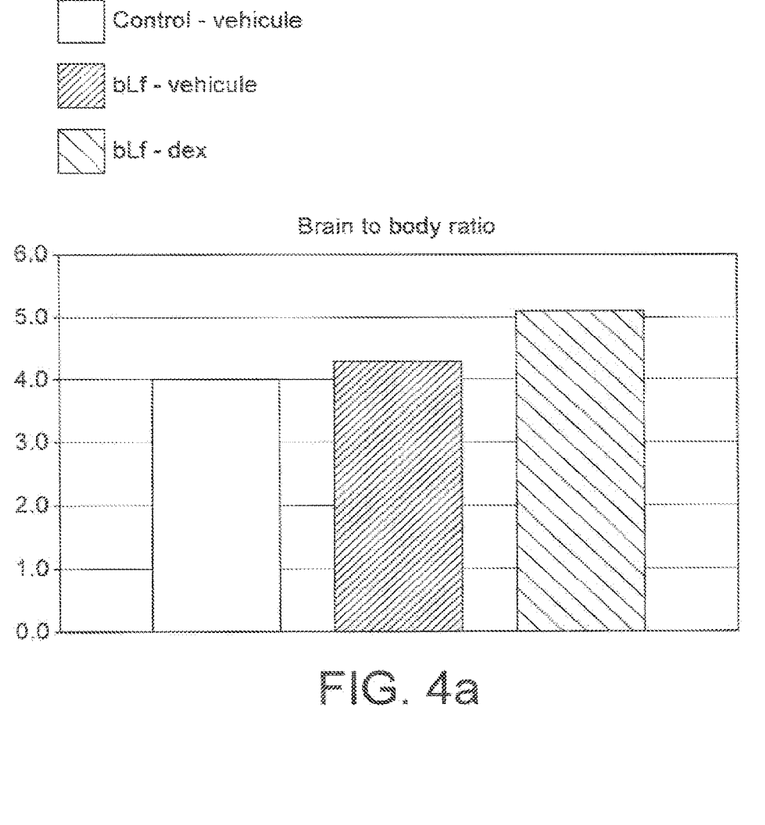
FIG. 4a shows the brain to body weight ratio at P1 in normal and IUGR rats. The brain to body weight ratio was found to be increased after lactoferrin administration, both in normal rats and even more in IUGR rats.
Figure 4B:
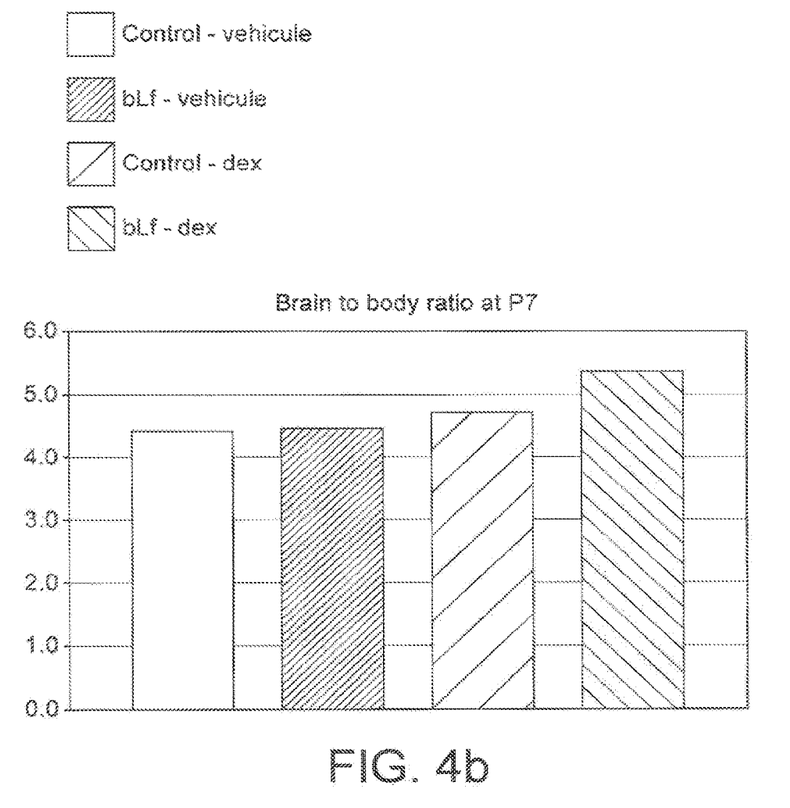
FIG. 4b shows the brain to body weight ratio at P7 in normal and IUGR rats. The brain to body weight ratio was found to be increased after lactoferrin administration, both in normal rats and even more in IUGR rats.
Figure 5:
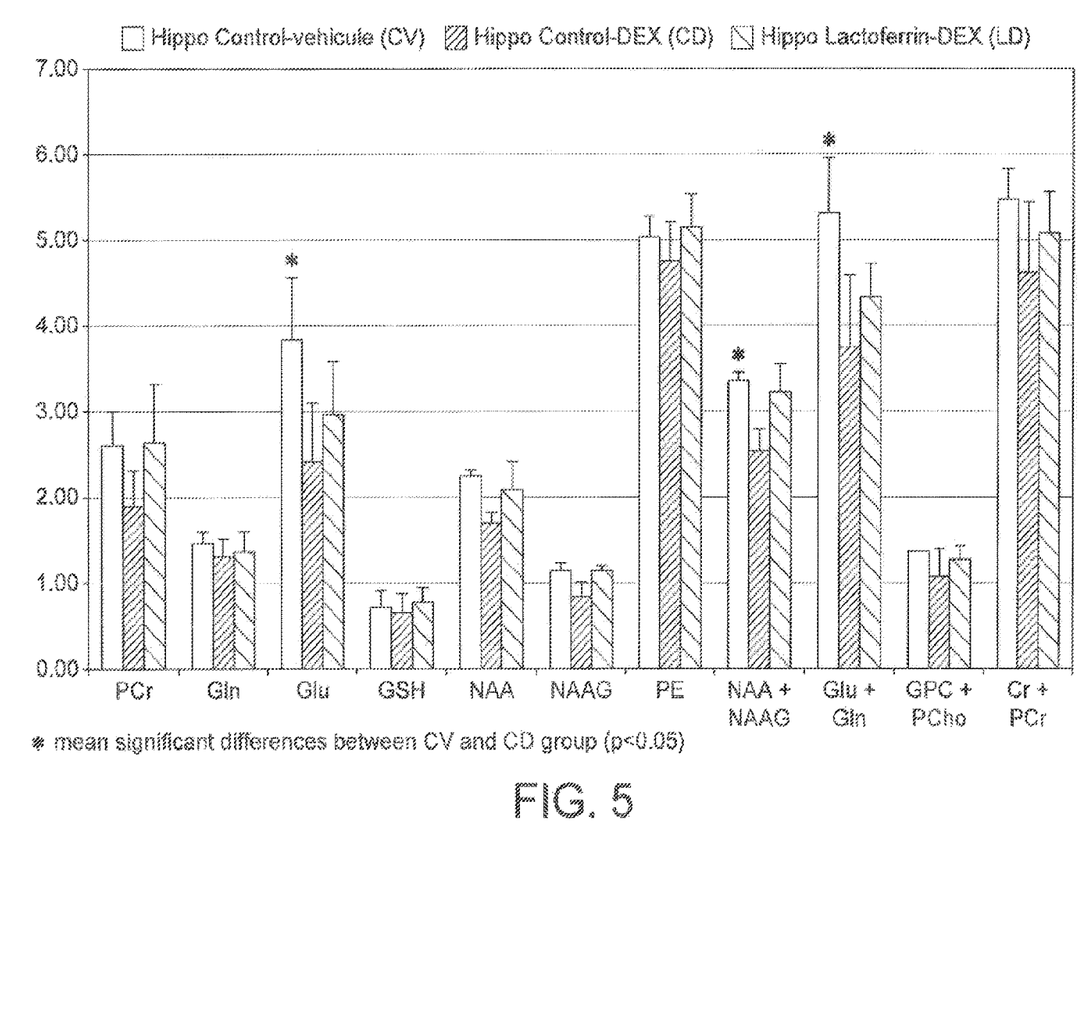
FIG. 5 shows the presence of several metabolic markers indicative for brain activity and development in the hippocampus of normal rats, IUGR rats and IUGR rats treated with lactoferrin at P7. Hippocampal activity is linked to learning and short term memory.
Figure 6:
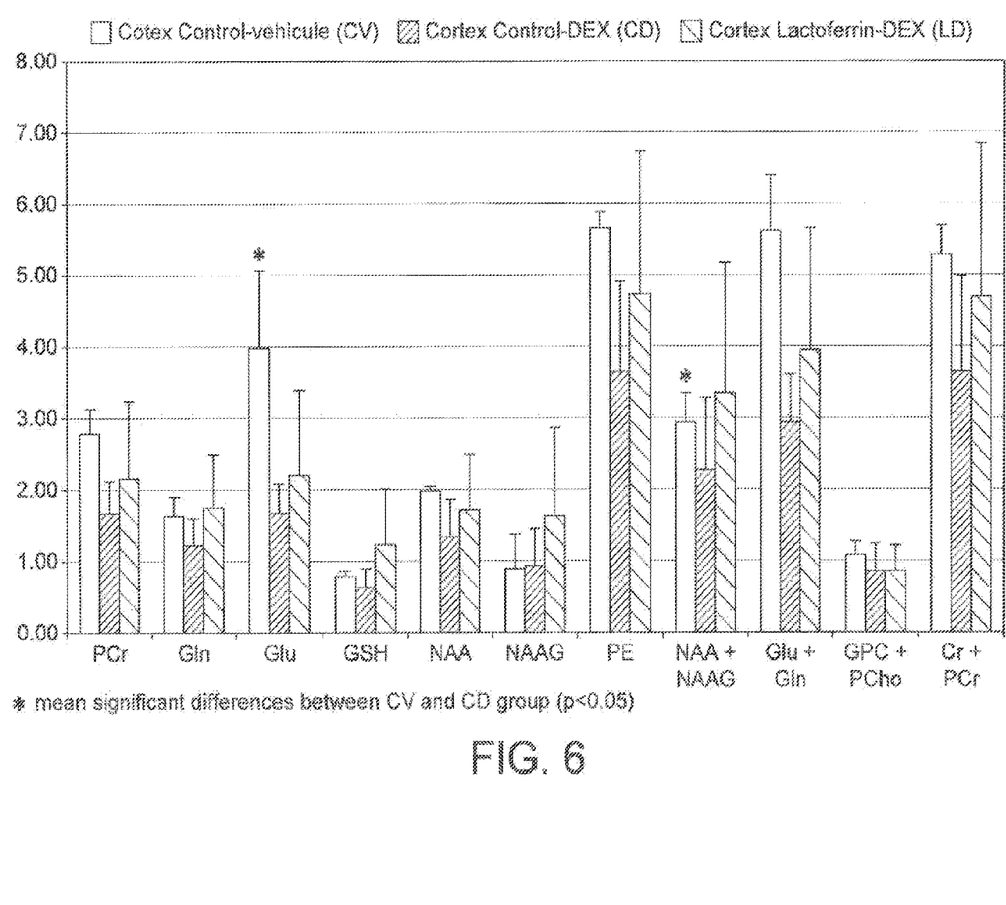
FIG. 6 shows the presence of several metabolic markers indicative for brain activity and development in the cortex of normal rats, IUGR rats and IUGR rats treated with lactoferrin at P7. Cortex activity is linked to long term memory.
Figure 7:
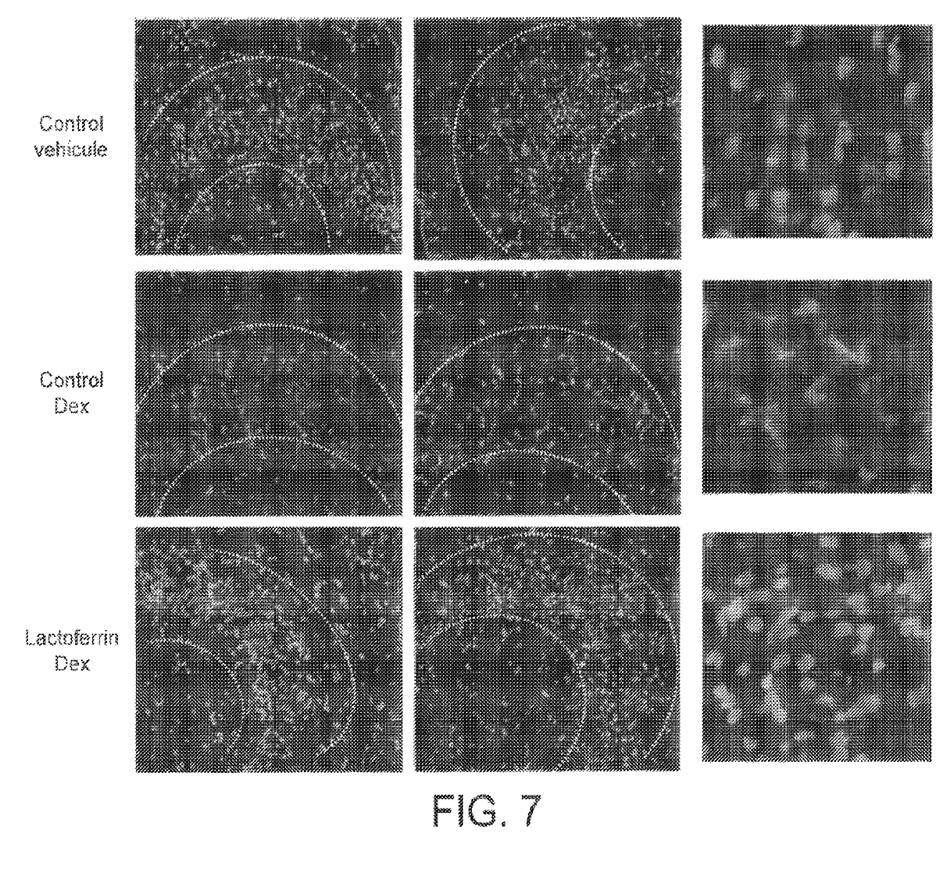
FIG. 7 shows the nuclei morphology in the CA2-CA3 field of the hippocampus after DAPI staining.
Figure 8:
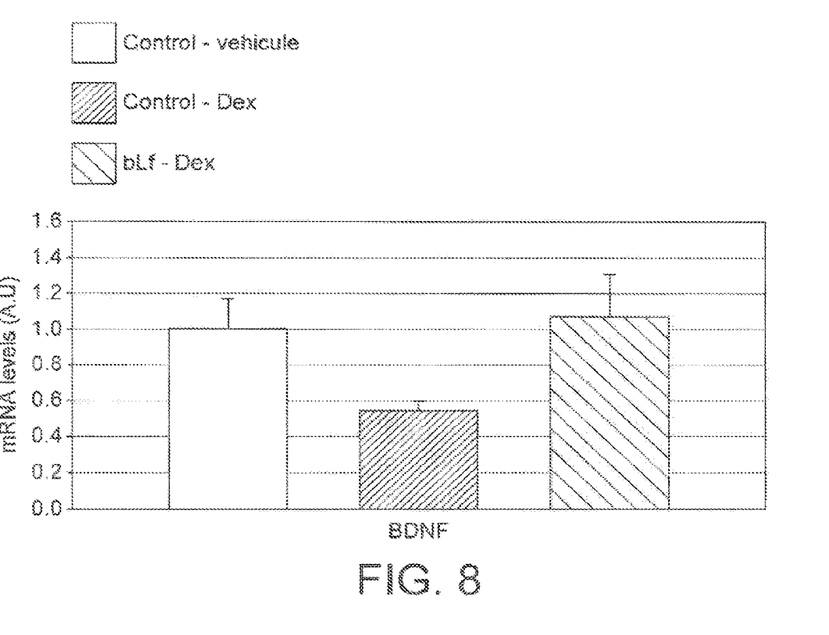
FIG. 8 shows theat lactoferrin supplementation also increased the gene expression of Brain derived neutrophic factor (BDNF).

The results were the following and are shown in FIG. 4.

The histological analysis revealed that LF supplementation Dex pup ($n=2$) has significant increased the Nuclei morphology and neuron density in the CA2-CA3 field of the hippocampus compared to the Dex control pup at P7. A decrease in neuronal density in the cortex at P7 suggests neuronal loss. The neuronal density is similar to the normal control vehicle group (FIG. 4). Lactoferrin given in this particular developmental time frame will influence neuronal density in the hippocampus and area of great vulnerability for undernutrition and stress related abnormalities. This implies that LF administration increases neuron survival and neuron protection, for example in a young IUGR rat.

The invention is claimed as follows:

1. A method for the treatment of intestinal neuropathies and disorders associated therewith comprising administering a composition comprising an ingestible composition comprising lactoferrin in a concentration of at least 0.1 g/100 kcal of the composition to an elderly individual in need of same.

2. A method for the treatment of impairments of the enteric nervous system comprising administering a composition comprising an ingestible composition comprising lactoferrin in a concentration of at least 0.1 g/100 kcal of the composition to an elderly individual in need of same.

3. A method for the repair of the enteric nervous system comprising administering a composition comprising an ingestible composition comprising lactoferrin in a concentration of at least 0.1 g/100 kcal of the composition to an elderly individual in need of same.

4. The method of claim 3, wherein the elderly individual has an intestinal neuropathy.

5. A method for the treatment of disorders linked to an impaired enteric nervous system comprising administering a composition comprising an ingestible composition comprising lactoferrin in a concentration of at least 0.1 g/100 kcal of the composition to an elderly individual in need of same.

6. The method of claim 5, wherein the disorder is selected from the group consisting of a low digestive and absorptive capacity, malnutrition, gastrointestinal reflux, intestinal dismotility, a slow intestinal transit, constipation, chronic intestinal pseudoobstruction, fecal incontinence, a weak intestinal barrier function, enteral feeding intolerance, gut discomfort, and hard stools.

* * * * *